US012433586B2

(12) United States Patent
Liao et al.

(10) Patent No.: US 12,433,586 B2
(45) Date of Patent: Oct. 7, 2025

(54) SAFETY MECHANISM FOR ENSURING DISPOSABLE USE OF AN INSTRUMENT

(71) Applicant: EZISURG (SUZHOU) MEDICAL CO. LTD., Jiangsu (CN)

(72) Inventors: Menghui Liao, Shanghai (CN); Lei Wang, Shanghai (CN); Chuangang Tang, Shanghai (CN); Jun Yang, Shanghai (CN); Minghui Bao, Shanghai (CN); Honglin Nie, Shanghai (CN)

(73) Assignee: Ezisurg (Suzhou) Medical Co. Ltd., Jiangsu (CN)

( * ) Notice: Subject to any disclaimer, the term of this patent is extended or adjusted under 35 U.S.C. 154(b) by 900 days.

(21) Appl. No.: 17/290,500

(22) PCT Filed: Nov. 1, 2019

(86) PCT No.: PCT/CN2019/114937
§ 371 (c)(1),
(2) Date: Nov. 29, 2021

(87) PCT Pub. No.: WO2020/088629
PCT Pub. Date: May 7, 2020

(65) Prior Publication Data

US 2023/0181188 A1 Jun. 15, 2023

(30) Foreign Application Priority Data

Nov. 2, 2018 (CN) ......................... 201811303644.2

(51) Int. Cl.
*A61B 17/072* (2006.01)
*A61B 90/00* (2016.01)
*A61B 17/00* (2006.01)

(52) U.S. Cl.
CPC ............ *A61B 17/072* (2013.01); *A61B 90/08* (2016.02); *A61B 2017/0023* (2013.01); *A61B 2017/07285* (2013.01); *A61B 2090/0814* (2016.02)

(58) Field of Classification Search
CPC ........ A61B 2017/07278; A61B 17/072; A61B 2090/0814; A61B 2017/07285; A61B 90/08

(Continued)

(56) References Cited

U.S. PATENT DOCUMENTS 7,328,828 B2 * 2/2008 Ortiz ................ A61B 17/07207 227/181.1
8,636,187 B2 * 1/2014 Hueil ................... A61B 17/072 227/176.1

(Continued)

FOREIGN PATENT DOCUMENTS

CN 102885641 A 1/2013
CN 103565486 A 2/2014

(Continued)

OTHER PUBLICATIONS

International Search Report and Written Opinion mailed Feb. 1, 2020 in International Application PCT/CN2019/114937.

(Continued)

*Primary Examiner* — Gloria R Weeks
(74) *Attorney, Agent, or Firm* — Fox Rothschild LLP

(57) ABSTRACT

The present disclosure relates to a safety mechanism comprising: a staple cartridge, a staple cartridge base, a sliding block, a cutter, and a staple anvil, wherein the staple cartridge base is centrally provided with an central track, a proximal end of the staple cartridge base is provided with a bias track, the bias track is in communication with a proximal end of the central track, a distal end of the bias track is (Continued)

provided with a blocking groove, and the sliding block is assembled at a proximal end of the staple cartridge; a first guide structure is provided on the cutter; the sliding block is provided with a second guide structure corresponding to the first guide structure of the cutter, and the second guide structure is capable of guiding the first guide structure to a central position from a biased position, so that the cutter enters the central track.

12 Claims, 3 Drawing Sheets

(58) Field of Classification Search
USPC ........................................................ 227/175.2
See application file for complete search history.

(56) References Cited

U.S. PATENT DOCUMENTS

| | | | | |
|---|---|---|---|---|
| 9,554,796 | B2 * | 1/2017 | Kostrzewski | A61B 90/08 |
| 2005/0222616 | A1 | 10/2005 | Rethy et al. | |
| 2007/0102475 | A1 | 5/2007 | Ortiz et al. | |
| 2013/0248577 | A1 | 9/2013 | Leimbach et al. | |
| 2013/0334284 | A1 | 12/2013 | Swayze et al. | |
| 2014/0203062 | A1 * | 7/2014 | Viola | A61B 90/08 227/175.1 |
| 2014/0263569 | A1 * | 9/2014 | Williams | A61B 17/105 227/180.1 |
| 2014/0291382 | A1 * | 10/2014 | Lloyd | A61B 17/07207 227/176.1 |
| 2015/0173745 | A1 * | 6/2015 | Baxter, III | A61B 17/068 227/176.1 |
| 2015/0230795 | A1 * | 8/2015 | Zheng | A61B 17/07207 227/176.1 |
| 2016/0310136 | A1 | 10/2016 | Gupta et al. | |
| 2020/0261075 | A1 * | 8/2020 | Boudreaux | A61B 90/08 |

FOREIGN PATENT DOCUMENTS

| | | | |
|---|---|---|---|
| CN | 103767751 | A | 5/2014 |
| CN | 204708912 | U | 10/2015 |
| CN | 105682570 | A | 6/2016 |
| CN | 105796145 | A | 7/2016 |
| CN | 209951320 | U | 1/2020 |

OTHER PUBLICATIONS

English translation of first Office Action mailed on Oct. 18, 2024 in CN201811303644.2.

Extended European Search Report mailed on Jul. 26, 2022 in EP 19879588.2.

* cited by examiner

SAFETY MECHANISM FOR ENSURING DISPOSABLE USE OF AN INSTRUMENT

CROSS REFERENCE TO RELATED APPLICATION

This application is a national stage application, filed under 35 U.S.C. § 371, of International Application PCT/CN2019/114937, filed on Nov. 1, 2019, entitled "ENSURING MECHANISM FOR ENSURING DEVICE MAY ONLY BE USED ONCE," which claims priority to Chinese Patent Application 201811303644.2 filed on Nov. 2, 2018 which are incorporated herein by reference in their entireties.

TECHNICAL FIELD

The present disclosure relates to the field of medical instruments, and in particular, to a safety mechanism for ensuring disposable use of a staple cartridge in a stapler.

BACKGROUND ART

The stapler is a main medical instrument that is medically used in place of conventional manual suture, and has the advantages of convenient in use, rapid suturing, tight suturing, moderate tightness, and fewer side effects and surgical complications.

Currently, schemes used in the stapler for times limiting are as follows: a scheme used for times limiting adopted by Johnson & Johnson is a manner of pressing a cutter by a spring sheet, wherein the spring sheet is connected to a staple cartridge base by means of electric welding.

This technical solution has an obvious defect that if the elastic force of the spring sheet fails or a welding spot falls off, this times limiting mechanism is vulnerable to failures, resulting in a failure of instrument or even death of patient. Covidien company adopts a times limiting mechanism placed in a staple casing inner tube, wherein a times limiting clamping piece is connected to a sleeve, wherein the sleeve is connected to a firing drive of the stapler, an initial state refers to that the times limiting clamping piece abuts against a guide rail in the staple casing inner tube under the action of a spring, when the firing drive drives the times limiting clamping structure to move forwards, the times limiting clamping piece is divorced from the rail, and when the firing drive is reset and performs firing again, the times limiting clamping piece then abuts against a boss in the staple casing inner tube. The defect of this technical solution is that the strength of a plastic inner tube and the times limiting clamping piece cannot be very high, and if a relatively great human force is encountered, there is a risk of damaging them, and the times limiting mechanism fails.

SUMMARY

For the shortcomings in the prior art, the technical problem to be solved in the present disclosure is to provide a safety mechanism for ensuring disposable use of a staple cartridge in a stapler, to ensure that the staple cartridge in the stapler can only be used once in surgery, and guarantee the patients' safety.

According to one aspect of the present disclosure, a safety mechanism for ensuring disposable use of a staple cartridge in a stapler is provided, including: the staple cartridge, a staple cartridge base, a sliding block, a cutter, and a staple anvil, wherein the staple cartridge base is centrally provided with an central track, a proximal end of the staple cartridge base is provided with a bias track, the bias track is in communication with a proximal end of the central track, a distal end of the bias track is provided with a blocking groove, and the sliding block is assembled at a proximal end of the staple cartridge; a first guide structure is provided on the cutter; the sliding block is provided with a second guide structure corresponding to the first guide structure of the cutter, and the second guide structure is capable of guiding the first guide structure to enter a central position from a biased position, so that the cutter enters the central track.

Further, a third guide structure provided separated from the first guide structure is further provided on the cutter.

Further, when the staple cartridge is assembled in the staple cartridge base, the sliding block is positioned between the staple cartridge base and the staple cartridge, and located in an initial position, and at a distal end of the cutter, and the first guide structure is in contact with the second guide structure.

Further, a bias structure is provided at a proximal end of the staple anvil, the bias structure is corresponding to the bias track of the staple cartridge base, and the bias structure guides the cutter to enter the bias track of the staple cartridge base. The bias structure is, for example, a bias boss.

Further, the cutter is fixedly connected at a distal end of a cutter bar assembly.

Further, the first guide structure is a guide protrusion; and the second guide structure is a guide surface.

Further, the guide surface is an inclined surface inclined in a direction from outside to a central axis of the staple cartridge base.

Further, at the initial position of the sliding block, the guide protrusion of the cutter is in contact with a proximal end of the guide surface of the sliding block. When the cutter continues moving forward, the guide protrusion of the cutter enters, under the guiding effect of the guide surface of the sliding block, the central track of the staple cartridge base.

Further, when the sliding block is not at the initial position, the cutter enters the bias track of the staple cartridge base due to restriction of the bias boss of the staple anvil, and when the cutter continues moving forwards, a buckle enters the blocking groove of the staple cartridge base, and is restricted from moving forwards.

Further, the third guide structure is a buckle.

Further, the guide protrusion and the buckle are provided at two sides of the cutter in a horizontal direction, respectively.

According to another aspect of the present disclosure, surgical instrument for ensuring disposable use of a staple cartridge is provided, including: the staple cartridge, a staple cartridge base, a sliding block, a cutter, and a staple anvil, wherein the staple cartridge base is centrally provided with an central track, a proximal end of the staple cartridge base is provided with a bias track, the bias track is in communication with a proximal end of the central track, a distal end of the bias track is provided with a blocking groove, and the sliding block is assembled at a proximal end of the staple cartridge; a first guide structure is provided on the cutter; the sliding block is provided with a second guide structure corresponding to the first guide structure of the cutter, and the second guide structure is capable of guiding the first guide structure to a central position from a biased position, so that the cutter enters the central track.

Further, the surgical instrument is a stapler.

Further, the stapler includes, but is not limited to, disposable stapler, reusable stapler, electric stapler, etc.

The safety mechanism for ensuring disposable use of a staple cartridge in a stapler in the present disclosure has a simple and effective structure, and once the safety mechanism takes effect, it is difficult to destroy it by human force, thus ensuring the patients' safety of using the instrument. The safety mechanism of the present disclosure can also prevent accidental firing of the cutter when it is unloaded (i.e. the staple cartridge is not loaded), so as to prevent the user from accidents.

BRIEF DESCRIPTION OF DRAWINGS

In order to more clearly illustrate technical solutions of the present disclosure, accompanying drawings which need to be used for description of the embodiments or the prior art will be introduced briefly below, and apparently, the accompanying drawings in the description below merely show some embodiments of the present disclosure, and those ordinarily skilled in the art still could obtain other accompanying drawings in light of these accompanying drawings, without paying any creative efforts.

DETAILED DESCRIPTION OF EMBODIMENTS

Technical solutions in the embodiments of the present disclosure will be described clearly and completely below in connection with accompanying drawings of the description, and apparently, the embodiments described are only some but not all embodiments of the present disclosure. All of other embodiments obtained by those ordinarily skilled in the art based on the embodiments of the present disclosure without any creative efforts shall fall within the scope of protection of the present disclosure.

The term "exemplary" is used herein to mean "serving as an example, instance, or illustration". Any implementation described herein as "exemplary" is not necessarily to be construed as being better than or superior to other implementations. Moreover, in the text, "proximal end", "proximal", and "rear" refer to an end proximate to an operator, and "distal end", "distal", and "front" refer to an end away from the operator.

For the sake of simplicity, the stapler is taken as an example to illustrate the instrument of the present disclosure. Those skilled in the art could understand that a safety mechanism for ensuring disposable use of an instrument in the present disclosure is not limited to the stapler. In other products such as closure and electric scalpel, the technology of the present disclosure may also be adopted.

For the safety mechanism for ensuring disposable use of a staple cartridge in a stapler in the present disclosure, the stapler includes an actuator located at a distal end, a controller located at a proximal end, and an extension tube located between the actuator and the controller. The extension tube is movably connected to a distal end of the controller, and a distal end of the extension tube is pivotably connected to a proximal end of the actuator, preferably by one or more hinges. The extension tube constitutes one connecting channel for transferring an action made by the controller to the actuator. The actuator includes a staple anvil assembly and a staple cartridge assembly that can clamp tissues therebetween.

Figure 1:
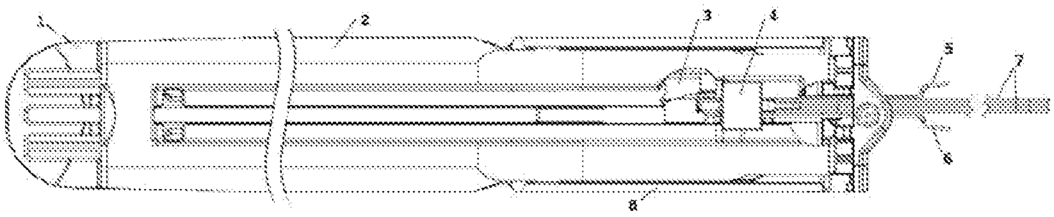
FIG. 1 is a schematic view of states of various parts when a sliding block 3 is at an initial position.

Specifically, the safety mechanism for ensuring disposable use of a staple cartridge in a stapler according to the present disclosure includes a staple cartridge 1, a staple cartridge base 2, a sliding block 3, a cutter 4, protective plates 5 and 6, a cutter bar assembly 7, and a staple anvil 8, wherein the staple cartridge base 2 is centrally provided with an central track, and the sliding block is provided on the staple cartridge base; with reference to FIG. 1, the cutter 4 is fixedly connected at a distal end of the cutter bar assembly 7.

Figure 7:
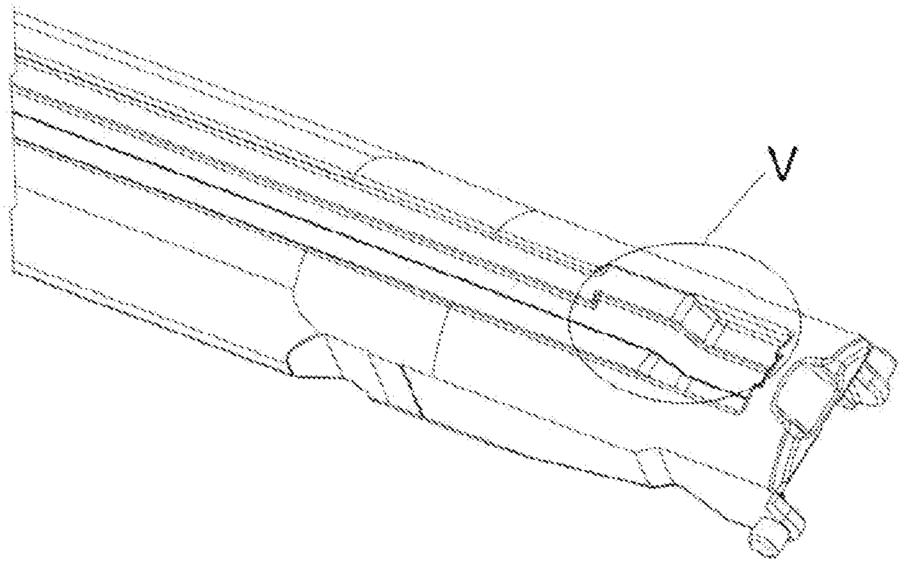
FIG. 7 is a structural schematic view of a bias track and a blocking groove of the staple cartridge base 2.

With reference to FIG. 7, a bias track is provided at a proximal end of the staple cartridge base 2, seeing V in FIG. 7, and the bias track is in communication with a proximal end of the central track of the staple cartridge base 2. A blocking groove is provided at a distal end of the bias track, seeing V in FIG. 7.

Figure 6:
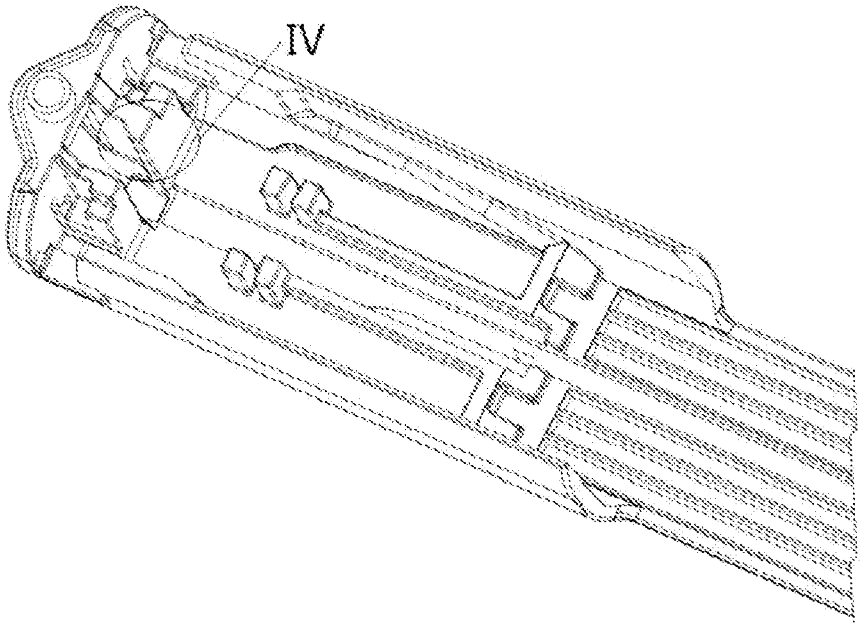
FIG. 6 is a schematic view of a bias boss of a staple anvil 8.

With reference to FIG. 6, a bias boss is provided at a proximal end of the staple anvil 8, seeing IV in FIG. 6, and the bias boss is corresponding to the bias track of the staple cartridge base 2.

Figure 4:
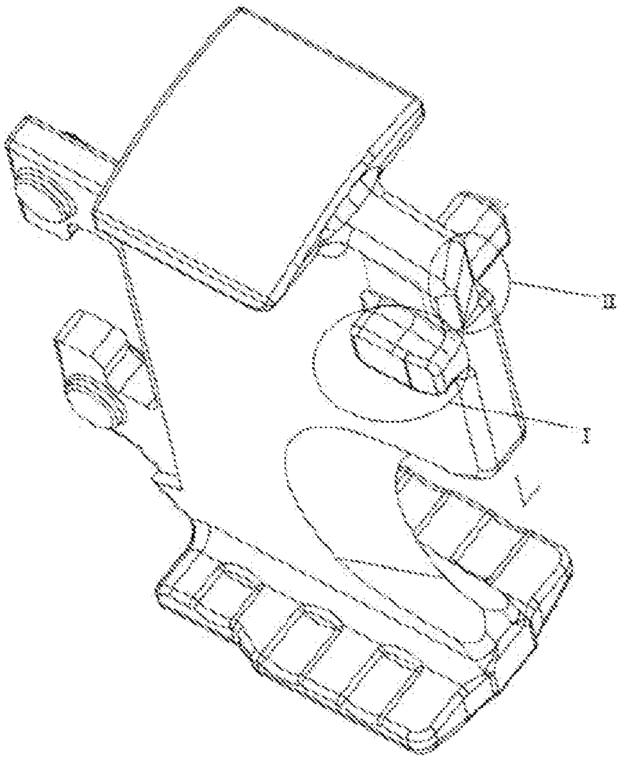
FIG. 4 is a schematic view of a guide surface and a buckle of the cutter 4.

With reference to FIG. 4, a guide protrusion is provided on the cutter 4, seeing I in FIG. 4; and the cutter 4 is further provided with a buckle, seeing II in FIG. 4.

Figure 5:
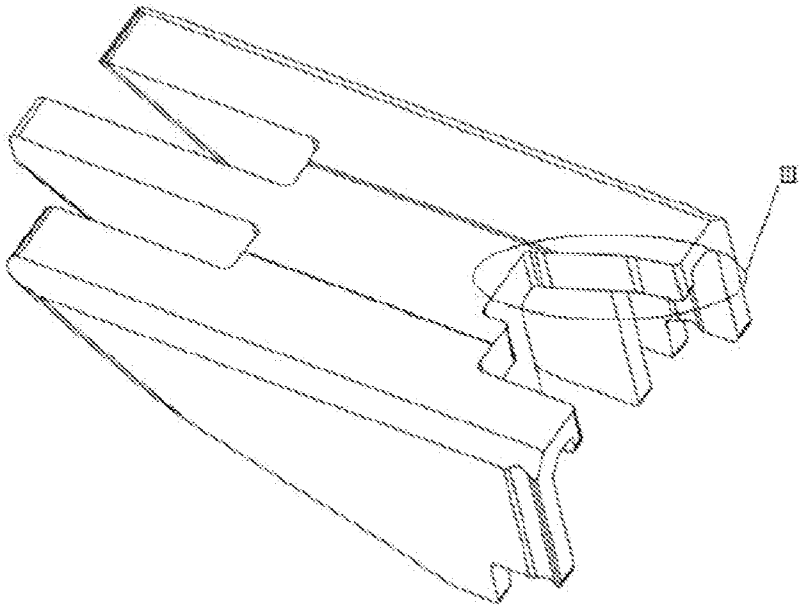
FIG. 5 is a structural schematic view of a guide surface of the sliding block 3.

With reference to FIG. 5, the sliding block 3 is provided with a guide surface corresponding to the guide protrusion of the cutter 4, seeing III in FIG. 5, and the guide surface is an inclined surface inclined in a direction from outside to a central axis of the staple cartridge base 2, so that the guide protrusion can be guided from a biased position to a central position where the guide protrusion may move forwards, so that the guide protrusion may enter the central track.

Figure 2:
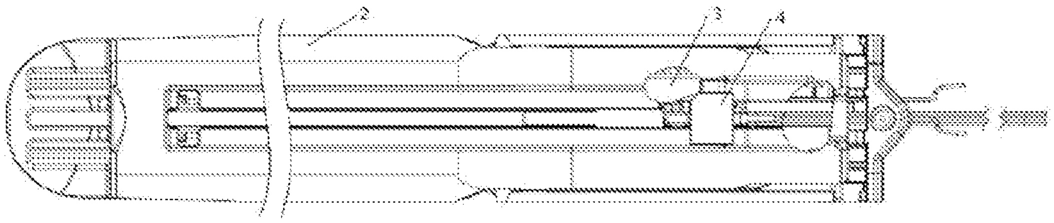
FIG. 2 is a schematic view of a state when a cutter 4 is guided by the sliding block 3 to enter an central track.

FIG. 1 is a structural schematic view of an embodiment of the present disclosure. The state in the figure is that the sliding block 3 is at an initial position. The sliding block 3 is assembled at the proximal end of the staple cartridge 1 before delivery, and when the staple cartridge 1 is assembled into the staple cartridge base 2, the sliding block 3 is positioned between the staple cartridge base and the staple cartridge, and located at the initial position, at the distal end of the cutter 4. At this time, the cutter bar assembly 7 is in contact with the bias boss (as shown by IV in FIG. 6) at the proximal end of the staple anvil 8, so that the cutter 4 is biased into the bias track of the staple cartridge base 2 (as V in FIG. 7), at this time, the guide protrusion (as I in FIG. 4) of the cutter 4 comes into contact with a proximal end of the guide surface (as III in FIG. 5) of the sliding block 3; when the cutter 4 and the cutter bar assembly 7 continue moving forward, the guide protrusion (as I in FIG. 4) of the cutter 4 enters the central track of the staple cartridge base under the guiding effect of the guide surface (as III in FIG. 5) of the sliding block 3, as in FIG. 2, at this time the cutter 4 may continue moving forwards.

Figure 3:
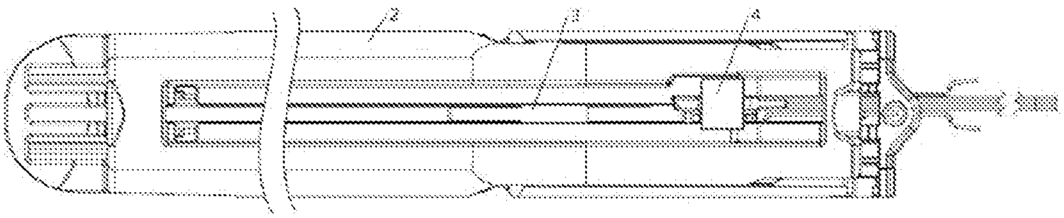
FIG. 3 is a schematic view of a state when the sliding block 3 is not at the initial position.

When the sliding block 3 is not at the initial position, as in FIG. 3, the cutter 4 enters the bias track of the staple cartridge base 2 due to restriction of the bias boss of the staple anvil 8, in this case, when the cutter 4 continues moving forwards without the restriction of the guide surface of the sliding block 3, the buckle (as II in FIG. 4) of the cutter 4 enters the blocking groove (as V in FIG. 7) of the staple cartridge base 2, and is restricted from moving forwards.

Specifically, the guide protrusion and the buckle on the cutter are provided at two sides of the cutter in a horizontal direction (i.e. a direction perpendicular to a central axis of the stapler), respectively.

The safety mechanism for ensuring disposable use of a staple cartridge in a stapler in the present disclosure has a simple and effective structure, and once the safety mechanism takes effect, it is difficult to destroy it by human force, thus ensuring the patients' safety of using the instrument.

The above-mentioned are preferred embodiments of the present disclosure, and it should be indicated that those ordinarily skilled in the art still could make improvements and modifications, without departing from the principle of the present disclosure, and all of these improvements and modifications also should be considered as the scope of protection of the present disclosure.

The invention claimed is:

1. A surgical instrument comprising:

a safety mechanism for ensuring disposable use of a staple cartridge which is assembled into a staple cartridge base;

the safety mechanism including:

a sliding block which is assembled at a proximal end of the staple cartridge;

a cutter which comes into contact with a proximal end of the sliding block when the sliding block is at an initial position; and a first guide structure provided on the cutter, a second guide structure provided on the sliding block and corresponding to the first guide structure, and a third guide structure provided on the cutter and separated from the first guide structure;

wherein the cutter is biased into a bias track of the staple cartridge base when the sliding block is at the initial position, and the second guide structure is configured to guide the first guide structure to a central position from a biased position, so that the cutter enters a central track of the staple cartridge base under guiding effect of the sliding block when the cutter continues moving forward; and wherein the cutter is biased into the bias track of the staple cartridge base when the sliding block is not at the initial position, and when the cutter continues moving forwards, the third guide structure enters a blocking groove of the staple cartridge base, so that the cutter is restricted from moving forwards.

2. The surgical instrument according to claim 1, further comprising a staple anvil, wherein the staple cartridge base is centrally provided with the central track, a proximal end of the staple cartridge base is provided with the bias track, the bias track is in communication with a proximal end of the central track, a distal end of the bias track is provided with the blocking groove, and the sliding block is assembled at a proximal end of the staple cartridge.

3. The surgical instrument according to claim 2, wherein when the staple cartridge is assembled in the staple cartridge base, the sliding block is positioned between the staple cartridge base and the staple cartridge, and located in an initial position, and at a distal end of the cutter, and the first guide structure is in contact with the second guide structure.

4. The surgical instrument according to claim 3, wherein a bias structure is provided at a proximal end of the staple anvil, the bias structure is corresponding to the bias track of the staple cartridge base, and the bias structure guides the cutter to enter the bias track of the staple cartridge base.

5. The surgical instrument according to claim 4, wherein the bias structure is a bias boss.

6. The surgical instrument according to claim 5, wherein the first guide structure is a guide protrusion, and the second guide structure is a guide surface, and the third guide structure is a buckle.

7. The surgical instrument according to claim 4, wherein the first guide structure is a guide protrusion; and the second guide structure is a guide surface, and the third guide structure is a buckle.

8. The surgical instrument according to claim 7, wherein the guide surface is an inclined surface inclined in a direction from outside to a central axis of the staple cartridge base.

9. The surgical instrument according to claim 7, wherein the guide protrusion and the buckle are provided at two sides of the cutter in a horizontal direction, respectively.

10. The surgical instrument according to claim 9, wherein at the initial position of the sliding block, the guide protrusion of the cutter is in contact with a proximal end of the guide surface of the sliding block; and when the cutter continues moving forward, the guide protrusion enters, under a guiding effect of the guide surface of the sliding block, the central track of the staple cartridge base.

11. The surgical instrument according to claim 9, wherein when the sliding block is not at the initial position, the cutter enters the bias track of the staple cartridge base due to restriction of the bias structure of the staple anvil.

12. The surgical instrument according to claim 1, wherein the cutter is fixedly connected at a distal end of a cutter bar assembly.

* * * * *